United States Patent [19]

Orth et al.

[11] 4,332,728
[45] Jun. 1, 1982

[54] PROCESS FOR THE PREPARATION OF BISACYL HYDRAZINES

[75] Inventors: Winfried Orth, Hassloch/Pfalz; Fritz W. Lange, Gauting; Werner Fickert, Mannheim-Seckenheim, all of Fed. Rep. of Germany

[73] Assignee: Rutgerswerke Aktiengesellschaft, Frankfurt am Main, Fed. Rep. of Germany

[21] Appl. No.: 224,129

[22] Filed: Jan. 12, 1981

[30] Foreign Application Priority Data

Feb. 23, 1980 [DE] Fed. Rep. of Germany ....... 3006807

[51] Int. Cl.³ ................. C07D 207/27; C07D 211/76; C07D 401/12
[52] U.S. Cl. .................................. 548/519; 546/188; 546/208; 548/550
[58] Field of Search ...................... 260/326.25, 326.43; 546/188, 208; 564/134

[56] References Cited

U.S. PATENT DOCUMENTS 3,417,114 12/1968 Kuceski ............................. 564/134
3,567,778 3/1971 Gavin ................................. 564/134
4,123,548 10/1978 Lange et al. .................... 260/326.43

OTHER PUBLICATIONS

De Feo et al., J. Org. Chem., vol. 28, pp. 2915–2917 (1963).
Wagner et al., Synthetic Organic Chemistry, (New York, 1953), pp. 568–569.
Smith, Open-Chain Nitrogen Compounds, vol. II, (W. A. Benjamin, Inc., New York, 1965), pp. 29–30.

*Primary Examiner*—Alton D. Rollins
*Attorney, Agent, or Firm*—Hammond & Littell, Weissenberger & Muserlian

[57] ABSTRACT

An improved process for the preparation of acyl hydrazides of the formula

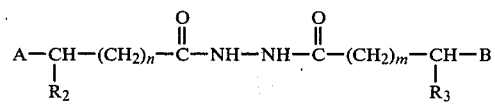

wherein A and B individually are a group of the formula

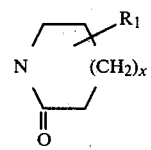

wherein $R_1$ is selected from the group consisting of hydrogen and alkyl of 1 to 4 carbon atoms, x is 0 or 1 and $R_2$ and $R_3$ are individually selected from the group consisting of hydrogen and alkyl of 1 to 4 carbon atoms and n and m are individually 0, 1, 2 or 3 by reacting a compound of the formula

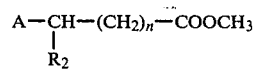

with a hydrazide of the formula

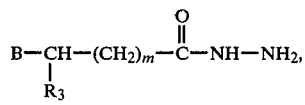

the improvement comprising effecting the reaction in the presence of at least one catalyst of the formula R'—OMe wherein R' is selected from the group consisting of hydrogen and alkyl of 1 to 4 carbon atoms and Me is an alkali metal.

7 Claims, No Drawings

PROCESS FOR THE PREPARATION OF BISACYL HYDRAZINES

STATE OF THE ART

N,N'-bis-acyl hydrazides are prepared by reacting an ester with a corresponding acyl hydrazide as described in German DOS No. 2,440,633 or German patent application Ser. No. P 27 45 907. A hydrazide of formula III is reacted with an alkyl ester of the formula

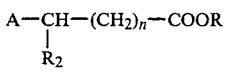

wherein R is alkyl of 1 to 4 carbon atoms, preferably methyl, but the yields of the process are uneconomically low, on the order of 5 to 55%.

OBJECTS OF THE INVENTION

It is an object of the invention to provide an improved, simple process for the preparation of acyl hydrazides of formula I in good yields and a high degree of purity.

This and other objects and advantages of the invention will become obvious from the following detailed description.

THE INVENTION

In the improved process of the invention for the preparation of acyl hydrazides of the formula

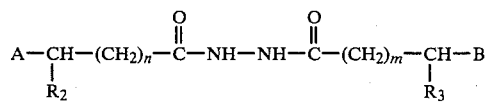

wherein A and B individually are a group of the formula

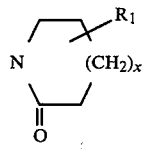

wherein $R_1$ is selected from the group consisting of hydrogen and alkyl of 1 to 4 carbon atoms, x is 0 or 1 and $R_2$ and $R_3$ are individually selected from the group consisting of hydrogen and alkyl of 1 to 4 carbon atoms and n and m are individually 0, 1, 2 or 3 by reacting a compound of the formula

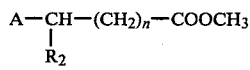

with a hydrazide of the formula

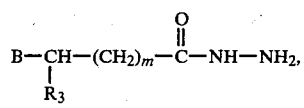

the improvement comprising effecting the reaction in the presence of at least one catalyst of the formula R'-OMe wherein R' is selected from the group consisting of hydrogen and alkyl of 1 to 4 carbon atoms and Me is an alkali metal. The said process results in substantially higher yields than the prior art process, on the average order of 70 to 85% of theory.

Examples of suitable catalysts are alkali metal hydroxides and alkoxides such as sodium hydroxide, potassium hydroxide, sodium methylate, potassium methylate, sodium ethylate, potassium ethylate, sodium isopropylate, lithium isopropylate, potassium sec.-butylate, potassium tert.-butylate, sodium tert.-butylate and sodium butylate. The amount of catalyst is not critical and may vary between 0.01 to 50 mole percent, preferably 0.01 to 1.0, most preferably 0.05 to 0.2 mole percent, based on the compound of formula II or III.

The compounds of formulae II and III are preferably reacted in substantially equimolar amounts of each or with a slight excess of about 0.1 to 0.4 moles of either one. The reaction may be effected in the absence of a solvent but is preferably effected in at least one inert organic solvent such as lower alkanols of 1 to 5 carbon atoms such as methanol or isopropanol or aromatic hydrocarbons such as toluene or xylene or mixtures thereof.

The reaction is most advantageously carried out at elevated temperatures such as 100° to 180° C., preferably 120° to 140° C. with the specific temperature depending on the specific catalyst used. In some instances, it might be advisable to first cool the reaction mixture and the reaction may be effected at normal pressure, subatmospheric pressure or superatmospheric pressure and may be effected under an inert atmosphere such as nitrogen.

The compounds of formula I are known to possess valuable pharmacological properties and may be used in psychotheraphy, for example and the process is particularly useful for the preparation of N,N'-bis-(pyrrolidin-2-one-1-acetyl)hydrazides.

The compounds of formula III can be prepared as described in German DOS 2,440,633 by the reaction of a compound of formula II with hydrazine and when the process is used to prepare symetrical bis-hydrazides, the compounds of formula III need not be isolated from the reaction mixture, but the additional amount of the compound of formula II is merely added thereto. In this latter embodiment, the alkali metal catalyst may be added to the initial mixture of hydrazine and the compound of formula II but preferably, the alkali metal catalyst is added to the mixture after the formation of the compound of formula III.

In the following examples there are described several preferred embodiments of the invention to illustrate the invention. However, it is to be understood that the invention is not intended to be limited to the specific embodiments.

EXAMPLE 1

N,N'-bis-(pyrrolidin-2-one-1-acetyl)-hydrazide

A mixture of 157 g (1 mole) of pyrrolidin-2-one-1-acetyl-hydrazide, 157 g (1 mole) of methyl pyrrolidin-2-one-1-acetate and 500 ml of xylene was heated to 100° C. and then a solution of 8.1 g (0.15 mole) of sodium methylate in 100 ml of methanol was added thereto dropwise with stirring whereby the methanol distilled off over a small column. Then, the mixture was heated with stirring at 130° C. ±1° C. for 24 hours while distilling off the methanol formed to maintain the temperature constant. The mixture was then cooled to 90° C.

and 150 ml of isopropanol were added thereto. The mixture was refluxed for one hour and was then cooled to room temperature. The mixture was vacuum filtered and the recovered product was rinsed 3 times with 150 ml of isopropanol and dried in vacuo at 60°–70° C. to obtain 242–245.6 g of N,N'bis-(pyrrolidin-2-one-1-acetyl)-hydrazide melting at 201°–203° C. The yield was 86 to 87% of theory.

EXAMPLES 2 TO 14

The procedure of Example 1 was repeated except the catalyst and solvent were changed to those reported in Table I. The amount of catalyst and the percentage of yield of N,N'-bis-(pyrrolidin-2-one-1-acetyl)-hydrazide are also reported in the Table.

TABLE I

| Example No. | Catalyst | Solvent | Mol. % | Yield % of theory |
|---|---|---|---|---|
| 2 | Sodium hydroxide | methanol | 0.15 | 76.3 |
| 3 | Potassium hydroxide | methanol | 0.15 | 78.7 |
| 4 | Potassium methylate | methanol | 0.10 | 85.3 |
| 5 | Potassium methylate | methanol | 0.15 | 87.2 |
| 6 | Sodium ethylate | ethanol | 0.12 | 83.8 |
| 7 | Sodium ethylate | none | 0.15 | 82.1 |
| 8 | Potassium ethylate | ethanol | 0.1 | 83.5 |
| 9 | Sodium isopropylate | isopropanol | 0.1 | 82.8 |
| 10 | Lithium isopropylate | methanol | 0.15 | 77.1 |
| 11 | Potassium sec.-butylate | sec.-butanol | 0.15 | 83.1 |
| 12 | Sodium tert.-butylate | none | 0.1 | 81.1 |
| 13 | Potassium tert.-butylate | none | 0.08 | 82.2 |
| 14 | Sodium butylate | none | 0.15 | 84.3 |

EXAMPLE 15

N,N'-bis-(pyrrolidin-2-one-1-acetyl)-hydrazide

A mixture of 157 g (1 mole) of pyrrolidin-2-one-1-acetyl hydrazide, 171 g (1 mole) of ethyl pyrrolidin-2-one-1-acetate and 500 ml of xylene was heated to 100° C. and then, a solution of 12.6 g (0.15 mole) of potassium ethylate in 150 ml of ethanol was added dropwise with stirring in proportion to the ethanol distilling off. Subsequently, the mixture was heated for 24 hours with stirring at 130°±1° C. while the ethanol formed by the reaction was distilled over a small column to keep the temperature constant. Then, the mixture was cooled to 90° C. and 150 ml of isopropanol were added thereto. The mixture was refluxed for one hour and was then cooled to room temperature. The mixture was vacuum filtered and the recovered product was washed 3 times with 150 ml of isopropanol and dried under vacuo at 60°–70° C. to obtain 233–241 g of N,N'-bis-(pyrrolidine-2-one-1-acetyl)-hydrazide melting at 202°–203° C. The yield was 82.5 to 85.3% of theory and the product was crystallized from ethanol for purification.

EXAMPLE 16

N,N'-bis-(5-methyl-pyrrolidin-2-one-1-acetyl)-hydrazide 16.8 g (0.15 mole) of potassium tert.-butylate were added portion wise with stirring to a mixture of 171 g (1 mole) of 5-methyl-pyrrolidin-2-one-1-acetyl-hydrazide, 171 g (1 mole) of methyl 5-methyl-pyrrolidin-2-one-1-acetate and 300 ml of xylene and the mixture was heated at 130°±1° C. while distilling of the methanol and tert.-butanol formed in the reaction to maintain the temperature constant. The mixture was cooled to 90° C. and 150 ml of isopropanol were added thereto. The mixture was refluxed with stirring for one hour and was then cooled to room temperature and vacuum filtered. The recovered product was rinsed 3 times with 150 ml of isopropanol and dried under vacuo at 60°–70° C. to obtain 245–258 g of N,N'-bis-(5-methyl-pyrrolidin-2-one-1-acetyl)-hydrazide melting at 181° C. The yield was 79–83% of theory.

Various modifications of the process may be made without departing from the spirit or scope thereof and it is to be understood that the invention is intended to be limited only as defined in the appended claims.

We claim:

1. In a process for the preparation of acyl hydrazides of the formula

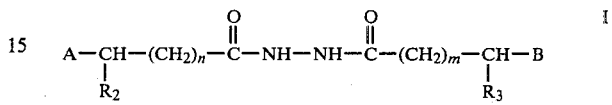

wherein A and B individually are a group of the formula

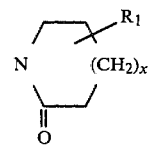

wherein $R_1$ is selected from the group consisting of hydrogen and alkyl of 1 to 4 carbon atoms, x is 0 or 1 and $R_2$ and $R_3$ are individually selected from the group consisting of hydrogen and alkyl of 1 to 4 carbon atoms and n and m are individually 0, 1, 2 or 3 by reacting a compound of the formula

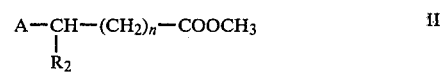

with a hydrazide of the formula

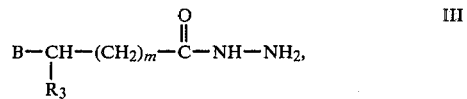

the improvement comprising effecting the reaction in the presence of at least one catalyst of the formula R'—OMe wherein R' is selected from the group consisting of hydrogen and alkyl of 1 to 4 carbon atoms and Me is an alkali metal.

2. The process of claim 1 wherein the amount of catalyst is 0.01 to 1.0 mole-percent based on the amount of the compound of formula II or III.

3. The process of claim 2 wherein the amount is 0.05 to 0.2 mole-percent.

4. The process of claim 1 wherein the reaction is effected at 100° to 180° C.

5. The process of claim 1 wherein the reaction is effected at 120° to 140° C.

6. The process of claim 1 wherein A and B are pyrrolidin-2-one, $R_2$ and $R_3$ are hydrogen and n and m are 0.

7. The process of claim 1 wherein the compound of formula III is formed by reacting a compound of formula II with hydrazine and the latter is reacted without isolation with another mole of the compound of formula II to form a symetrical bishydrazide.

* * * * *